(12) United States Patent
Feng et al.

(10) Patent No.: US 12,017,206 B2
(45) Date of Patent: Jun. 25, 2024

(54) PREPARATION METHOD OF Cu—Pd—CeO2/γ—Al2O3@NP CATALYST AND SYNTHESIS METHOD OF BENZOPYRAZINE COMPOUNDS

(71) Applicant: ZHEJIANG UNIVERSITY OF TECHNOLOGY, Zhejiang (CN)

(72) Inventors: Feng Feng, Zhejiang (CN); Xiaonian Li, Zhejiang (CN); Lingling Guo, Zhejiang (CN); Yanxia Sun, Zhejiang (CN); Chunshan Lu, Zhejiang (CN); Qunfeng Zhang, Zhejiang (CN); Jiatong Jin, Zhejiang (CN); Xiaoliang Xu, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 101 days.

(21) Appl. No.: 17/955,012

(22) Filed: Sep. 28, 2022

(65) Prior Publication Data
US 2023/0095076 A1 Mar. 30, 2023

(30) Foreign Application Priority Data
Sep. 30, 2021 (CN) .......................... 202111160999.2

(51) Int. Cl.
| | | |
|---|---|---|
| *C07D 241/42* | (2006.01) | |
| *B01J 21/04* | (2006.01) | |
| *B01J 23/89* | (2006.01) | |
| *B01J 37/00* | (2006.01) | |
| *B01J 37/02* | (2006.01) | |
| *B01J 37/04* | (2006.01) | |
| *B01J 37/08* | (2006.01) | |

(52) U.S. Cl.
CPC ............. *B01J 23/894* (2013.01); *B01J 21/04* (2013.01); *B01J 37/009* (2013.01); *B01J 37/024* (2013.01); *B01J 37/04* (2013.01); *B01J 37/088* (2013.01); *C07D 241/42* (2013.01)

(58) Field of Classification Search
CPC ....... C07D 241/42; B01J 23/894; B01J 21/04; B01J 37/009; B01J 37/024; B01J 37/04; B01J 37/088
See application file for complete search history.

(56) References Cited

FOREIGN PATENT DOCUMENTS

| | | |
|---|---|---|
| CN | 106311305 A | 1/2017 |
| CN | 112657527 A | 4/2021 |
| JP | 2000-309578 A | 11/2000 |
| WO | WO-2013/191661 A1 | 12/2013 |

OTHER PUBLICATIONS

Guimaraes, J Phys Chem B, 2003, vol. 107, 4311-4319. (Year: 2003).*
Xie, Green Chem, 2015, vol. 17, 279-284. (Year: 2015).*
Chakrabarti, Green Chem, 2019, vol. 21, 1999-2004. (Year: 2019).*
Feng, Feng et al., "Cu—Pd/γ—Al2O3 Catalyzes the One-Pot Synthesis of 2-Methylquinoline by Nitrobenzene and Ethanol Reaction", Scientia Sinica Chimica, 2011, pp. 914-924, Issue No. 5.
Mierczynski, P. et al., "Methanol Synthesis Using Copper Catalysts Supported on CeO2—Al2O3 Mixed Oxide," Fibre Chemistry, Nov. 2016, pp. 271-275, vol. No. 48, Issue No. 4.
Chiguru Srinivas et al., *Efficient, convenient and reusable polyaniline-sulfate salt catalyst for the synthesis of quinoxaline derivatives*, Journal of Molecular Catalysis A: Chemical 265 (2007), 227-230.
T. B Nguyen et al., *Sodium Sulfide: A Sustainable Solution for Unbalanced Redox Condensation Reaction between o-Nitroanilines and Alcohols Catalyzed by an Iron-Sulfur System*, Synthesis 2015, 47: 1741-1748.
Feng Xie et al., *Efficient synthesis of quinoxalines from 2-nitroanilines and vicinal diols via a rutheniumcatalyzed hydrogen transfer strategy*, The Royal Society of Chemistry, Green Chemistry, www.rsc.org/greenchem, 2014, 17: 279-284.

(Continued)

*Primary Examiner* — D Margaret M Seaman
(74) *Attorney, Agent, or Firm* — Muncy, Geissler, Olds & Lowe, P.C.

(57) ABSTRACT

A preparation method of Cu—Pd—CeO$_2$/γ-Al$_2$O$_3$@NP catalyst and a synthesis method of benzopyrazine compounds. The preparation method of the Cu—Pd—CeO$_2$/γ-Al$_2$O$_3$@NP catalyst comprises the following steps: (1) preparing a CeO$_2$/γ-Al$_2$O$_3$ carrier; (2) preparing a CeO$_2$/γ-Al$_2$O$_3$@NP carrier; (3) preparing the Cu—Pd—CeO$_2$/γ-Al$_2$O$_3$@NP catalyst by impregnation method. A one-pot method for synthesizing benzopyrazine compounds of formula (III) includes using an o-nitroaniline compound of formula (I) and an aliphatic diol compound of formula (II) as raw materials, carrying out the one-pot synthesis of the benzopyrazine compound of formula (III) under solvent-free condition and under the combined action of the Cu—Pd—CeO$_2$/γ-Al$_2$O$_3$@NP catalyst prepared by the method and an alkali. The Cu—Pd—CeO$_2$/γ-Al$_2$O$_3$@NP catalyst increases the number of basic sites by doping N and P, and meanwhile loads CeO$_2$ to assist in the extraction of protons, thereby improving the dehydrogenation activity and product selectivity.

13 Claims, No Drawings

(56) References Cited

OTHER PUBLICATIONS

K. Chakrabarti et al.,*Cooperative Iridium Complex Catralyzed Synthesis of Quinonalines, Benzimidiazoles and Quinazolines in Water, Green Chem.*, 2019, DOI: 10.1039/C8GC03744B, Green Chemistry, 2019, 21: 1999-2004.

S. Shee et al. *Cobalt Complex Catalyzed Atom-Economical Synthesis of Quinoxaline, Quinoline and 2-Alkylaminoquinoline Derivatives, Chem. Commun.*, 2018, DOI: 10.1039/C8CC02366B, 2018, 54: 6883-6886.

Sujan Shee et al., *Nickel-Catalyzed Direct Synthesis of Quinoxalines from 2-Nitroanilines and Vicinal Diols: Identifying Nature of the Active Catalyst*, The Journal of Organic Chemistry, 2020, 85: 2775-2784.

Dibyajyoti Panja et al., *Application of a reusable Co-based nanocatalyst in alcohol dehydrogenative coupling strategy: Synthesis of quinoxaline and imine scaffolds*, Catalysis Communications, Elsevier B.V., 2020, 137: 105927, https://doi.org/10.1016/j.catcom.2020.105927.

\* cited by examiner

PREPARATION METHOD OF Cu—Pd—CeO2/γ—Al2O3@NP CATALYST AND SYNTHESIS METHOD OF BENZOPYRAZINE COMPOUNDS

FIELD OF THE INVENTION

The invention relates to a preparation method of a Cu—Pd—CeO$_2$/γ-Al$_2$O$_3$@NP catalyst and a method for synthesizing benzopyrazine compounds by utilizing the catalyst.

BACKGROUND OF THE INVENTION

Benzopyrazine, also known as quinoxaline, is an important class of nitrogen-containing organic heterocyclic compounds, and its derivatives are important intermediates in organic drug synthesis. They have a wide range of pharmacological and biological activities, such as antibacterial, antiviral, anti-cancer, anti-tumor, etc.; therefore, the synthesis of benzopyrazine compounds has attracted much attention.

The traditional synthesis method of benzopyrazine and its derivatives is the condensation reaction of an ortho-dicarbonyl compound with high activity and an ortho-diamine. A paper [Chiguru Srinivas, Chebolu Naga Sesha Sai Pavan Kumar, Vaidya Jayathirtha Rao, Srinivasan Palaniappan, 2006, 265 (2007): 227-230] reported a synthetic method of quinazoline by using polyaniline sulfate as a catalyst, 1,2-dichloroethane as a solvent and glyoxal and o-phenylenediamine as raw materials, and stirring at room temperature for 30 minutes, and the yield can reach 85%. A paper [Thanh Binh Nguyen, Ludmila Ermolenko, Ali Al-Mourabit, 2015, 47: 1741-1748] reported that ferric chloride and sodium sulfide were used as catalysts, water was used as solvent, after stirring for 24 hours at 140-150° C. and under nitrogen atmosphere, benzopyrazine was synthesized from o-nitroaniline and ethylene glycol with a yield of 67%; 2,3-dimethylene was synthesized from o-nitroaniline and 2,3-butanediol as raw materials benzopyrazine, the yield can reach 75%. The method uses o-nitroaniline as a raw material, which reduces the cost of the raw material, but the product yield is not high. A paper [Feng Xie, Min Zhang, Huanfeng Jiang, Mengmeng Chen, Green Chemistry, 2015, 17: 279-284] reported that ruthenium carbonyl was used as catalyst, 1,3-bis(diphenylphosphine)propane was used as ligand, cesium hydroxide monohydrate was used as base promoter, tert-amyl alcohol was used as solvent, the reaction was carried out at 140-150° C. and under nitrogen atmosphere, and after stirred for 24 hours, 2-methylbenzopyrazine was synthesized from o-nitroaniline and 1,2-propanediol with a yield of 74%, and 2,3-dimethylbenzopyrazine was synthesized from o-nitroaniline and 2,3-butanediol with a yield of 82%. The method also uses o-nitroaniline as a raw material to reduce the raw material cost, but the product yield is still not high. A paper [Kaushik Chakrabarti, Milan Maji, Sabuj Kundu, Green Chemistry, 2019, 21: 1999-2004] reported that iridium with 2-hydroxypyridyl complex was used as a catalysts, potassium hydroxide was used as an alkali assistant, water was used as solvent, the reaction was carried out at 120° C., and after stirred for 24 hours, 2-methylbenzopyrazine was synthesized from o-nitroaniline and 1,2-propanediol with a yield of 87%, and 2,3-dimethylbenzopyrazine was synthesized from o-nitroaniline and 2,3-butanediol with a yield of 90%. The yield of this method is considerable, but the homogeneous catalyst used is not conducive to industrial production. A paper [Sujan Shee, Kasturi Ganguli, Kalipada Jana, Sabuj Kundu, 2018, 54: 6883-6886] reported that Co(NNN) complex was used as a catalysts, cesium hydroxide monohydrate was used as an alkali promoter, toluene was used as a solvent, the reaction temperature was 150° C., and after stirring for 24 h, 2-methylbenzopyrazine was synthesized from o-nitroaniline and 1,2-propanediol with a yield of up to 75% and 2,3-dimethylbenzopyrazine was synthesized from o-nitroaniline and 2,3-butanediol with a yield of as high as 96%. The method also has a considerable yield, but still uses a homogeneous catalyst that is unfavorable for industrial production, and uses an environmentally unfriendly organic solvent. A paper [Sujan Shee, Dibyajyoti Panja, Sabuj Kundu, 2020, 85: 2775-2784] reported that nickel bromide complexed with phenanthroline was used as a catalyst, cesium hydroxide monohydrate was used as a base assistant, toluene was used as a solvent, the reaction was carried out under argon atmosphere and at 150° C., after stirred for 24 h, 2-methylbenzopyrazine was synthesized from o-nitroaniline and 1,2-propanediol with a yield of 93% and 2,3-dimethylbenzopyrazine was synthesized from o-nitroaniline and 2,3-butanediol with a yield of as high as 94%. The yield of this method is considerable, but it uses a homogeneous catalyst that is unfavorable for industrial production, and requires a large amount of environmentally unfriendly organic solvent for a small amount of reactants. A paper [Dibyajyoti Panja, Bhaskar Paul, Bhuvaneshwari Balasubramaniam, Raju K. Gupta, Sabuj Kundu, 2020, 137: 105927] reported that carbon-supported cobalt with phenanthroline was used as a catalyst, cesium hydroxide monohydrate was used as an alkali promoter, toluene was used as a solvent, the reaction was carried out under argon atmosphere and at 150° C., and after stirring for 24 h, 2-methylbenzopyrazine was synthesized from o-nitroaniline and 1,2-propanediol with a yield of 93% and 2,3-dimethylbenzopyrazine was synthesized from o-nitroaniline and 2,3-butanediol with a yield of as high as 96%. The yield of this method is considerable, and a heterogeneous catalyst that is beneficial to industrial production is used, but a small amount of reactants needs a large amount of environmentally unfriendly organic solvent.

To sum up, among the existing technologies for synthesizing quinoxaline and its derivatives by chemical methods, some use expensive 1,2-dicarbonyl compounds and aromatic 1,2-diamines as raw materials; some use o-nitroaniline and aliphatic diol as raw materials, and these synthetic methods usually adopt transition metal complexes as catalysts, which causes separation and recovery of the catalysts to be difficult, the equipment requirements are high, and meanwhile there are disadvantages of high reaction temperature, long reaction time and high energy consumption. Although these methods have made great progress in expanding substrate types, optimizing catalysts and reaction conditions, improving the yield of benzopyrazine and its derivatives, simplifying reaction steps, and reducing environmental pollution, there are still problems such as using expensive raw materials and low product yields, and most of the methods use complex homogeneous catalysts, which are not conducive to industrial production; a small number of methods using heterogeneous catalysts also use a large amount of environmentally unfriendly organic solvents. Therefore, up to now, benzopyrazine or substituted benzopyrazine is still prepared by condensation with expensive 1,2-dicarbonyl compound and aromatic 1,2-diamine as raw materials, not only there are many reaction steps, but also product separation is cumbersome for most methods.

Therefore, it is necessary to find an efficient and environmentally friendly method for synthesizing benzopyrazine and its derivatives from o-nitroaniline compounds and aliphatic diols under the action of a solid catalyst.

SUMMARY OF THE INVENTION

The first technical problem to be solved by the present invention is to provide a preparation method of a Cu—Pd—CeO$_2$/γ-Al$_2$O$_3$@NP catalyst.

The second technical problem to be solved by the present invention is to provide a one-pot method for efficient synthesis of benzopyrazine and its derivatives with o-nitroaniline compounds and aliphatic diol compounds as raw materials under the combined action of Cu—Pd—CeO$_2$/γ-Al$_2$O$_3$@NP catalyst and alkali.

In order to solve the above-mentioned technical problems, the present invention adopts the following technical solutions:

In the first aspect, the present invention provides a preparation method of a Cu—Pd—CeO$_2$/γ-Al$_2$O$_3$@NP catalyst, in the Cu—Pd—CeO$_2$/γ-Al$_2$O$_3$@NP catalyst, the total loading amounts of N and P is 1.2%~4.8%, the loading amount of Cu is 0.5%~5 wt %, the loading amount of Pd is 0.5%~5 wt %, and the loading amount of Ce is 5%~15 wt %; the preparation method comprises the following steps:

(1) mixing a certain amount of γ-Al$_2$O$_3$ with deionized water, stirring the mixture to obtain a slurry, heating the slurry to 70-90° C., then adding a corresponding amount of a solution of cerium-containing compound, subjecting the mixture to stirring and impregnation at a constant temperature of 70-90° C. for 2~6 h, adding ammonia water dropwise to adjust the pH value of the solution to 9~10, continuing to stir the resulting solution at the constant temperature for 2~6 h, cooling it to room temperature and filtering it, washing the filter cake with deionized water until the filtrate becomes neutral, drying it at 80~120° C. for 5~9 h in the air, and then calcining it at 600~800° C. for 2~4 h in the air to obtain a CeO$_2$/γ-Al$_2$O$_3$ carrier;

(2) mixing a certain amount of the CeO$_2$/γ-Al$_2$O$_3$ carrier with an aqueous solution of ammonium phosphate, subjecting the mixture to stirring and impregnation at 30~50° C. for 1~3 h, then drying it at 80~120° C. for 5~9 h in the air, and then calcining the dried product at 400~600° C. for 1~3 h in the air to obtain a CeO$_2$/γ-Al$_2$O$_3$@NP carrier;

(3) mixing a certain amount of the CeO$_2$/γ-Al$_2$O$_3$@NP carrier with deionized water, stirring the mixture to obtain a slurry, heated it to 60~100° C., then adding certain amounts of a palladium-containing compound solution and a copper-containing compound solution, subjecting the mixture to stirring and impregnation at a constant temperature for 3~7 h ; cooling it to room temperature, adding an alkaline solution dropwise to adjust the pH value to 8~10, stirring the resulting solution at the constant temperature for 0.5~1.5 h, filtering it, washing the filter cake with deionized water until the filtrate becomes neutral; dry it at 80~120° C. in the air for 5~9 h; then calcining the dried product at 200~300° C. for 2~6 h in the air, and finally reducing the calcined product with hydrogen at 200~300° C. for 1~3 h, thereby obtaining the Cu—Pd—CeO$_2$/γ-Al$_2$O$_3$@NP catalyst.

The content of each element in the Cu—Pd—CeO$_2$/γ-Al$_2$O$_3$@NP catalyst of the present invention is calculated based on the utilization rate of each element in the preparation process being 100%, and the loading amount is calculated by mass percentage of the element relative to γ-Al$_2$O$_3$. Preferably, in the Cu—Pd—CeO$_2$/γ-Al$_2$O$_3$@NP catalyst, the loading amount of Pd is 1-5 wt %, more preferably 5 wt %; the loading amount of Cu is 1-5 wt %, more preferably 3.5%; and the loading amount of Ce is 5~15 wt %, more preferably 10%.

Preferably, the palladium-containing compound is H$_2$PdCl$_4$, Pd(CH$_3$COO)$_2$ or Pd(NO$_3$)$_2$; the copper-containing compound is Cu(NO$_3$)$_2$ or CuCl$_2$; the cerium-containing compound is CeCl$_3$ or Ce(OH)$_3$.

Preferably, in step (1), the feeding ratio of γ-Al$_2$O$_3$ to deionized water is 5 g:35-45 mL.

Preferably, in step (1), the concentration of the cerium-containing compound solution is 0.04-0.06 g/mL in terms of the concentration of Ce.

Preferably, in step (2), the concentration of the aqueous ammonium phosphate solution is 0.002-0.0025 g/mL. The feeding amount of the aqueous solution can be determined by the required P+N loading amounts.

Preferably, in step (3), the feeding ratio of the CeO$_2$/γ-Al$_2$O$_3$@NP carrier to deionized water, calculated as the feeding ratio of γ-Al$_2$O$_3$ to deionized water, is 5g:35-45 mL.

Preferably, in step (3), the concentration of the palladium-containing compound solution is 0.04-0.05 g/mL in terms of the concentration of Pd, and the concentration of the copper-containing compound solution is 0.04-0.05 g/mL in terms of the concentration of Cu.

Preferably, in step (3), the alkaline solution is 0.05~0.15 g/ml NaOH aqueous solution, 0.05~0.15 g/ml NaHCO$_3$ aqueous solution or 0.05~0.15 g/ml Na$_2$CO$_3$ aqueous solution.

In the second aspect, the present invention provides a one-pot method for synthesizing benzopyrazine compounds of formula (III), and the method comprises: using an o-nitroaniline compound of formula (I) and an aliphatic diol compound of formula (II) as raw materials, carrying out the one-pot synthesis of the benzopyrazine compound of formula (III) under solvent-free condition and under the combined action of the Cu—Pd—CeO$_2$/γ-Al$_2$O$_3$@NP catalyst and an alkali;

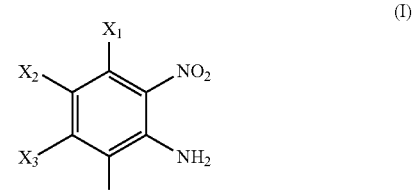

(I)

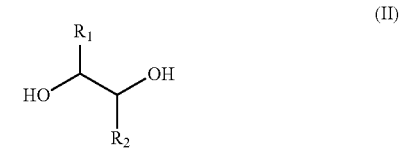

(II)

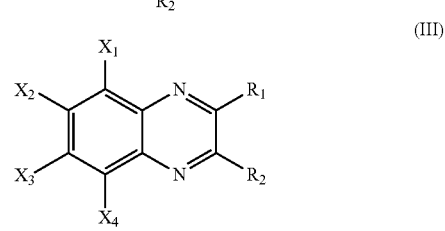

(III)

wherein, $X_1$, $X_2$, $X_3$, $X_4$ are each independently hydrogen, methyl, ethyl or methoxy; $R_1$, $R_2$ are each independently hydrogen, methyl or ethyl.

In the synthesis of the benzopyrazine compounds of the present invention, the mass ratio of the Cu—Pd—CeO$_2$/γ-Al$_2$O$_3$@NP catalyst to the o-nitroaniline compound is 1:5~20, preferably 1:10.

In the synthesis of the benzopyrazine compounds of the present invention, the molar ratio of the o-nitroaniline compound:aliphatic diol compound:alkali is 1:5~15:0.5~2, preferably 1:10:1.

In the synthesis of the benzopyrazine compounds of the present invention, the reaction temperature is 70-90° C., and the reaction time is 6-12 hours. Further, the reaction temperature is preferably 75-85° C.

In the synthesis of the benzopyrazine compounds of the present invention, the alkali is preferably KOH.

In the synthesis of the benzopyrazine compounds of the present invention, the reaction is carried out in the air.

Specifically, the one-pot method for synthesizing benzopyrazine compounds comprises: first, putting Cu—Pd—CeO$_2$/γ-Al$_2$O$_3$@NP, the o-nitroaniline compound of formula (I), the aliphatic diol of formula (II)) and the alkali into a three-necked flask reactor, controlling the temperature in the reactor at 75~85° C. to carry out the reaction for 6~12 h, after the reaction is completed, separating the reaction materials by filtration to obtain the catalyst (the catalyst can be used repeatedly) and a filtrate, and subjecting the filtrate to extraction, distillation or rectification to obtain the benzopyrazine compound.

By adopting the synthesis method of the present invention, the conversion rate of the raw material o-nitroaniline compound can reach up to 100%, and the yield of the target product benzopyrazine compound can reach up to 98%.

The beneficial effects of the present invention are as follows:

(1) The Cu—Pd—CeO$_2$/γ-Al$_2$O$_3$@NP catalyst described in the present invention increases the number of basic sites by doping N and P, and meanwhile loads CeO$_2$ to assist in the extraction of protons, thereby improving the catalytic dehydrogenation activity. The present invention constructs a supported metal solid catalyst with high activity, good stability and easy separation.

(2) Compared with traditional industrial production, the method for synthesizing benzopyrazine and its derivatives of the present invention simplifies production process, combines multiple steps of industrial production into one-pot reaction, and uses low-cost raw materials at the same time to reduce production costs.

(3) Compared with the current existing synthetic routes, the method for synthesizing benzopyrazine and its derivatives of the present invention does not use environmentally unfriendly organic solvents, nor does it need to use expensive alkali while achieving high product yields.

(4) The method for synthesizing benzopyrazine and its derivatives of the present invention adopts Cu—Pd—CeO$_2$/γ-Al$_2$O$_3$@NP catalyst as the catalyst, which shortens the reaction time, reduces the reaction temperature, reduces the reaction energy consumption, significantly improves the product selectivity, and makes the reaction process not consume transition metal and precious metal, the reuse easy and the industrial production conducive.

DETAILED DESCRIPTION OF THE INVENTION

The following specific examples illustrate the technical solutions of the present invention, but the protection scope of the present invention is not limited thereto.

Examples 1 to 3 are examples of preparing supported metal solid catalysts:

Example 1

5 g of γ-Al$_2$O$_3$ (aladdin #A102091) were mixed with 35 mL of deionized water and stirred to obtain a slurry, the slurry was heated to 70° C. in a water bath, 6.25 ml of Ce(OH)$_3$ solution (0.04 g Ce/ml) were added dropwise, the mixture was subjected to stirring and impregnation at 70° C. for 2 h, then ammonia water (25-28%) was added dropwise to adjust the pH value to between 9 and 10, then the temperature of the solution was maintained and the solution was stirred for another 2 hours; then the resulting reaction mixture was cooled to room temperature and filtered, and the filter cake was washed with deionized water until the filtrate became neutral; then the filter cake was dried in air atmosphere at 80° C. for 5 h and then calcined at 600° C. for 2 h in air atmosphere to obtain CeO25 wt %/γ-Al$_2$O$_3$; CeO25 wt %/γ-Al$_2$O$_3$ was then added into 40 ml of 0.002 g/ml ammonium phosphate aqueous solution, the mixture was subjected to stirring and impregnation at 30° C. for 1 h and then dried at 80° C. for 5 h, and the dried product was calcined at 400° C. for 1 h to obtain a CeO25 wt %/γ-Al$_2$O$_3$@NP carrier; CeO25 wt %/γ-Al$_2$O$_3$@NP was then mixed with 35 mL of deionized water and stirred to obtain a slurry, the slurry was heated to 60° C. in a water bath, 4.375 ml of Pd(C$_2$H$_3$O$_2$)$_2$ solution (0.04 g Pd/ml) and 1.875 ml of CuCl$_2$ solution (0.04 g Cu/ml) were added dropwise respectively, the mixture was subjected to stirring and impregnation at a constant temperature of 60° C. for 3 h, cooled to 25° C., then added dropwise with 0.1 g/ml NaHCO$_3$ aqueous solution to adjust the pH value to between 8 and 10, then stirred for 0.5 h and filtered, and the filter cake was washed with deionized water until the filtrate became neutral, dried at 80° C. for 5 h in air atmosphere, calcined at 200° C. for 2 h in air atmosphere, and finally reduced in hydrogen atmosphere at 200° C. for 1 h to obtain a Cu1.5 wt %-Pd3.5 wt %-CeO25 wt %/γ-Al$_2$O$_3$@NP catalyst.

Example 2

5 g of γ-Al$_2$O$_3$ (aladdin #A102091) were mixed with 40 mL of deionized water and stirred to obtain a slurry, the slurry was heated to 80° C. in a water bath, 10 ml of CeCl$_3$ solution (0.05 g Ce/ml) were added dropwise, the mixture was subjected to stirring and impregnation at 80° C. for 4 hours, then ammonia water (25-28%) was added dropwise to adjust the pH value to between 9 and 10, then the temperature of the solution was maintained and the solution was stirred for another 4 hours; then the resulting reaction mixture was cooled to room temperature and filtered, and the filter cake was washed with deionized water until the filtrate became neutral; then the filter cake was dried in air atmosphere at 100° C. for 7 h and then calcined at 700° C. for 3 h in air atmosphere to obtain CeO10 wt %/γ-Al$_2$O$_3$; CeO10 wt %/γ-Al$_2$O$_3$ was then added into 32 ml of 0.0025 g/ml ammonium phosphate aqueous solution, the mixture was subjected to stirring and impregnation at 40° C. for 2 h and then dried at 100° C. for 7 h, and the dried product was calcined at 500° C. for 2 h to obtain a CeO10 wt %/γ-Al$_2$O$_3$@NP carrier; CeO10 wt %/γ-Al$_2$O$_3$@NP was mixed with 40 mL of deionized water and stirred to obtain a slurry, the slurry was heated to 80° C. in a water bath, 5 ml of H$_2$PdCl$_4$ solution (0.05 g Pd/ml) and 3.5 ml of Cu(NO$_3$)$_2$ solution (0.05 g Cu/ml) were added dropwise respectively, the mixture was subjected to stirring and impregnation at a constant temperature of 80° C. for 5 h, cooled to 25° C. and then added dropwise with 0.1 g/ml $Na_2CO_3$ aqueous solution to adjust the pH value to between 8 and 10, then the mixture was stirred for 1 h and filtered, and the filter cake was washed with deionized water until the filtrate became neutral, dried at 100° C. for 7 h in air atmosphere, calcined at 250° C. for 4 h in air atmosphere, and finally reduced in hydrogen atmosphere at 250° C. for 2 h to obtain a Cu3.5 wt %-Pd5 wt %-$CeO_2$10 wt %/γ-$Al_2O_3$@NP catalyst.

Example 3

5 g of γ-$Al_2O_3$ (aladdin #A102091) were mixed with 45 mL of deionized water and stirred to obtain a slurry, the slurry was heated to 90° C. in a water bath, 12.5 ml of $CeCl_3$ solution (0.06 g Ce/ml) were added dropwise, the mixture was subjected to stirring and impregnation at 90° C. for 6 hours, then ammonia water (25-28%) was added dropwise to adjust the pH value to between 9 and 10, then the temperature of the solution was maintained and the solution was stirred for another 6 hours; then the resulting reaction mixture was cooled to room temperature and filtered, and the filter cake was washed with deionized water until the filtrate became neutral; then the filter cake was dried in air atmosphere at 120° C. for 9 h and then calcined at 800° C. for 4 h in air atmosphere to obtain CeO15 wt %/γ-$Al_2O_3$; CeO10 wt %/γ-$Al_2O_3$ was then added into 32 ml of 0.0025 g/ml ammonium phosphate aqueous solution, the mixture was subjected to stirring and impregnation at 50° C. for 3 h and then dried at 120° C. for 9 h, and the dried product was calcined at 600° C. for 3 h to obtain a CeO15 wt %/γ-$Al_2O_3$@NP carrier; CeO15 wt %/γ-$Al_2O_3$@NP was then mixed with 45 mL of deionized water and stirred to obtain a slurry, the slurry was heated to 100° C. in a water bath, 5 ml of $Pd(NO_3)_2$ solution (0.05 g Pd/ml) and 5 ml of $Cu(NO_3)_2$ solution (0.05 g Cu/ml) were added dropwise respectively, the mixture was subjected to stirring and impregnation at a constant temperature of 100° C. for 7 h, cooled to 25° C. and then added dropwise with 0.1 g/ml NaOH aqueous solution to adjust the pH value to between 8 and 10, then the mixture was stirred for 1.5 h and filtered, and the filter cake was washed with deionized water until the filtrate became neutral, dried at 120° C. for 9 h in air atmosphere, calcined at 300° C. for 6 h in air atmosphere, and finally reduced in hydrogen atmosphere at 300° C. for 3 h to obtain a Cu5 wt %-Pd5 wt %-$CeO_2$15 wt %/γ-$Al_2O_3$@NP catalyst.

Examples 4-14 used the Cu—Pd—$CeO_2$/γ-$Al_2O_3$@NP catalysts obtained by the above-mentioned preparation methods for the synthesis of benzopyrazine compounds:

Examples 4-6

Examples 4-6 investigated the reaction results of one-pot synthesis of benzopyrazine compounds from o-nitroaniline and various aliphatic diols.

0.2 g of the catalyst prepared in Example 2 (Cu3.5 wt %-Pd5 wt %-$CeO_2$10 wt %/γ-$Al_2O_3$@NP), 2 g of o-nitroaniline, 8 ml of an aliphatic diol and 0.8 g of potassium hydroxide were put into a three-necked flask reactor. The mixture was heated to 80° C. and started to stir (1000 r/min), after stirred at the constant temperature for 6 h, the reaction was stopped, and the reaction solution was cooled to room temperature and filtered to separate the catalyst. The filtrate was extracted and then analyzed by gas chromatography, and the experimental results are shown in Table 1.

TABLE 1

The experimental results of one-pot reaction of o-nitroaniline and different aliphatic diols

| example | aliphatic diol | conversion rate (%) | product | selectivity (%) |
|---|---|---|---|---|
| 4 | ethanediol | 100 | benzopyrazine | 98.3 |
| 5 | 1,2-propanediol | 100 | 2-methyl benzopyrazine | 94.7 |
| 6 | 2,3-butanediol | 100 | 2,3-dimethyl benzopyrazine | 93.1 |

Example 7

Example 7 investigated the effect of increasing the amount of catalyst to improve the yield of benzopyrazine.

0.4 g of the catalyst prepared in Example 2 (Cu3.5 wt %-Pd5 wt %-CeO210 wt %/γ-Al2O3@NP), 2 g of o-nitroaniline, 8 ml of ethanediol and 0.8 g of potassium hydroxide were put into a three-necked flask reactor. The mixture was heated to 80° C. and started to stir (1000 r/min), after stirred at the constant temperature for 6 h, the reaction was stopped, and the reaction solution was cooled to room temperature and filtered to separate the catalyst. The filtrate was extracted and then analyzed by gas chromatography, and the conversion rate of o-nitroaniline was 100%, the selectivity of the target product benzopyrazine is 97.5%.

Examples 8-10

Examples 8-10 investigated the reaction results of one-pot synthesis of benzopyrazine compounds with ethanediol and different o-nitroaniline compounds.

0.2 g of the catalyst prepared in Example 2 (Cu3.5 wt %-Pd5 wt %-$CeO_2$10 wt %/γ-$Al_2O_3$@NP), 2 g of an o-nitroaniline compound, 8 ml of ethanediol and 0.8 g of potassium hydroxide were put into a three-necked flask reactor. The mixture was heated to 80° C. and started to stir (1000 r/min), after stirred at the constant temperature for 6 h, the reaction was stopped, and the reaction solution was cooled to room temperature and filtered to separate the catalyst. The filtrate was extracted and then analyzed by gas chromatography, and the experimental results are shown in Table 2.

TABLE 2

The experimental result of one-pot reaction of ethylene glycol and different o-nitroaniline compounds

| example | o-nitroaniline compound | conversion rate (%) | product | selectivity (%) |
|---|---|---|---|---|
| 8 | 4-methyl-2-nitroaniline | 100 | 6-methyl-quinoxaline | 90.9 |
| 9 | 4-ethyl-2-nitroaniline | 100 | 6-ethyl-quinoxaline | 89.6 |
| 10 | 3-methyl-2-nitroaniline | 100 | 5-methyl-quinoxaline | 86.2 |

Examples 11-14

Examples 11-14 investigated the reaction results of one-pot synthesis of benzopyrazine from ethanediol and o-nitroaniline under the action of different catalysts.

A catalyst, 2 g of o-nitroaniline, 8 ml of ethanediol and 0.8 g of potassium hydroxide were put into a three-necked flask reactor, wherein the catalyst is respectively the catalyst prepared by Example 1, 2 or 3 and the catalyst recovered after the reaction of Example 4, and the amount of the catalyst is 0.2 g. The mixture was heated to 80° C. and started to stir (1000 r/min), after stirred at the constant temperature for 6 h, the reaction was stopped, and the reaction solution was cooled to room temperature and filtered to separate the catalyst. The filtrate was extracted and then analyzed by gas chromatography, and the experimental results are shown in Table 3, where the target product is benzopyrazine.

TABLE 3

The experimental results of one-pot reaction of ethanediol and o-nitroaniline under the action of different catalysts

| example | catalyst | conversion rate (%) | selectivity (%) |
|---|---|---|---|
| 11 | example 1 | 100 | 94.5 |
| 12 | Example 2 | 100 | 98.3 |
| 13 | Example 3 | 100 | 96.1 |
| 14 | catalyst recovered from Example 4 | 100 | 97.2 |

Comparative Example 1

5 g of γ-Al2O3 (aladdin #A102091) were mixed with 40 mL of deionized water and stirred to obtain a slurry, the slurry was heated to 80° C. in a water bath, 5 ml of $H_2PdCl_4$ solution (0.05 g Pd/ml) and 3.5 ml of $Cu(NO_3)_2$ solution (0.05 g Cu/ml) were added dropwise respectively, the mixture was subjected to stirring and impregnation at a constant temperature of 80° C. for 5 h, cooled to 25° C. and then added dropwise with 0.1 g/ml $Na_2CO_3$ aqueous solution to adjust the pH value to between 8 and 10, then the mixture was stirred for 1 h and filtered, and the filter cake was washed with deionized water until the filtrate became neutral, dried at 100° C. for 7 h in air atmosphere, calcined at 250° C. for 4 h in air atmosphere, and finally reduced in hydrogen atmosphere at 250° C. for 2 h to obtain a Cu3.5 wt %-Pd5 wt %/γ-$Al_2O_3$ catalyst.

Comparative Example 2

5 g of γ-$Al_2O_3$ (aladdin #A102091) were mixed with 40 mL of deionized water and stirred to obtain a slurry, the slurry was heated to 80° C. in a water bath, 10 ml of $CeCl_3$ solution (0.05 g Ce/ml) were added dropwise, the mixture was subjected to stirring and impregnation at 80° C. for 4 hours, then ammonia water (25-28%) was added dropwise to adjust the pH value to between 9 and 10, then the temperature of the solution was maintained and the solution was stirred for another 4 hours; then the resulting reaction mixture was cooled to room temperature and filtered, and the filter cake was washed with deionized water until the filter liquor became neutral; then the filter cake was dried in air atmosphere at 100° C. for 7 h and then calcined at 700° C. for 3 h in air atmosphere to obtain CeO10 wt %/γ-$Al_2O_3$; $CeO_2$10 wt %/γ-$Al_2O_3$ was then mixed with 40 mL of deionized water and stirred to obtain a slurry, the slurry was heated to 80° C. in a water bath, 5 ml of $H_2PdCl_4$ solution (0.05 g Pd/ml) and 3.5 ml of $Cu(NO_3)_2$ solution (0.05 g Cu/ml) were added dropwise respectively, the mixture was subjected to stirring and impregnation at a constant temperature of 80° C. for 5 h, cooled to 25° C. and then added dropwise with 0.1 g/ml $Na_2CO_3$ aqueous solution to adjust the pH value to between 8 and 10, then the mixture was stirred for 1 h and filtered, and the filter cake was washed with deionized water until the filtrate became neutral, dried at 100° C. for 7 h in air atmosphere, calcined at 250° C. for 4 h in air atmosphere, and finally reduced in hydrogen atmosphere at 250° C. for 2 h to obtain the Cu3.5 wt %-Pd5 wt %-$CeO_2$10 wt %/γ-$Al_2O_3$ catalyst.

Comparative Example 3

5 g of γ-$Al_2O_3$ (aladdin #A102091) were mixed with 32 ml of 0.0025 g/ml ammonium phosphate aqueous solution, the mixture was subjected to stirring and impregnation at 40° C. for 2 h and dried at 100° C. for 7 h, and the dried product was calcined at 500° C. for 2 h to obtain a γ-$Al_2O_3$@NP carrier; γ-$Al_2O_3$@NP was then mixed with 40 mL of deionized water and stirred to obtain a slurry, the slurry was heated to 80° C. in a water bath, 5 ml of $H_2PdCl_4$ solution (0.05 g Pd/ml) and 3.5 ml of $Cu(NO_3)_2$ solution (0.05 g Cu/ml) were added dropwise respectively, the mixture was subjected to stirring and impregnation at a constant temperature of 80° C. for 5 h, cooled to 25° C. and then added dropwise with 0.1 g/ml $Na_2CO_3$ aqueous solution to adjust the pH value to between 8 and 10, then the mixture was stirred for 1 h and filtered, and the filter cake was washed with deionized water until the filtrate became neutral, dried at 100° C. for 7 h in air atmosphere, calcined at 250° C. for 4 h in air atmosphere, and finally reduced in hydrogen atmosphere at 250° C. for 2 h to obtain a Cu3.5 wt %-Pd5 wt %/γ-$Al_2O_3$@NP catalyst.

Comparative Example 4

5 g of γ-$Al_2O_3$ (aladdin #A102091) were mixed with 40 mL of deionized water and stirred to obtain a slurry, the slurry was heated to 80° C. in a water bath, 10 ml of $CeCl_3$ solution (0.05 g Ce/ml) were added dropwise, the mixture was subjected to stirring and impregnation at 80° C. for 4 hours, then ammonia water (25-28%) was added dropwise to adjust the pH value to between 9 and 10, and the temperature of the solution was maintained and stirred for another 4 hours; then the resulting reaction mixture was cooled to room temperature and filtered, and the filter cake was washed with deionized water until the filtrate became neutral; then the filter cake was dried in an air atmosphere at 100° C. for 7 h and then calcined at 700° C. for 3 h in an air atmosphere to obtain CeO10 wt %/γ-$Al_2O_3$, CeO10 wt %/γ-$Al_2O_3$ was then added into 32 ml of 0.0025 g/ml ammonium phosphate aqueous solution, the mixture was subjected to stirring and impregnation at 40° C. for 2 h and dried at 100° C. for 7 h, and the dried product was calcined at 500° C. for 2 h to obtain a CeO10 wt %/γ-$Al_2O_3$@NP carrier, CeO10 wt %/γ-$Al_2O_3$@NP was then mixed with 40 mL of deionized water and stirred to obtain a slurry, the slurry was heated to 80° C. in a water bath, 5 ml of $H_2PdCl_4$ solution (0.05 g Pd/ml) were added dropwise, the mixture was subjected to stirring and impregnation at a constant temperature of 80° C. for 5 h, cooled to 25° C. and then added dropwise with 0.1 g/ml $Na_2CO_3$ aqueous solution to adjust the pH value to between 8 and 10, then the mixture was stirred for 1 h and filtered, and the filter cake was washed with deionized water until the filtrate became neutral, dried at 100° C. for 7 h in air atmosphere, calcined at 250° C. for 4 h in air atmosphere, and finally reduced in hydrogen atmosphere at 250° C. for 2 h to obtain a Pd5 wt %-$CeO_2$10 wt %/γ-$Al_2O_3$@NP catalyst.

Comparative Example 5

5 g of γ-$Al_2O_3$ (aladdin #A102091) were mixed with 40 mL of deionized water and stirred to obtain a slurry, the slurry was heated to 80° C. in a water bath, 10 ml of CeCl₃ solution (0.05 g Ce/ml) were added dropwise, the mixture was subjected to stirring and impregnation at 80° C. for 4 hours, then ammonia water (25-28%) was added dropwise to adjust the pH value to between 9 and 10, and the temperature of the solution was maintained and the solution was stirred for another 4 h; then the resulting reaction mixture was cooled to room temperature and filtered, and the filter cake was washed with deionized water until the filtrate became neutral; then the filter cake was dried in an air atmosphere at 100° C. for 7 h and then calcined at 700° C. for 3 h in an air atmosphere to obtain CeO10 wt %/γ-Al₂O₃, CeO10 wt %/γ-Al₂O₃ was added into 32 ml of 0.0025 g/ml ammonium phosphate aqueous solution, the mixture was subjected to stirring and impregnation at 40° C. for 2 h and dried at 100° C. for 7 h, and the dried product was calcined at 500° C. for 2 h to obtain a CeO10 wt %/γ-Al₂O₃@NP carrier; CeO10 wt %/γ-Al₂O₃@NP was then mixed with 40 mL of deionized water and stirred to obtain a slurry, the slurry was heated to 80° C. in a water bath, 3.5 ml of Cu(NO₃)₂ solution (0.05 g Cu/ml) were added dropwise respectively, the mixture was subjected to stirring and impregnation at a constant temperature of 80° C. for 5 h, cooled to 25° C. and then added dropwise with 0.1 g/ml Na₂CO₃ aqueous solution to adjust the pH value to between 8 and 10, then the mixture was stirred for 1 h and filtered, and the filter cake was washed with deionized water until the filtrate became neutral, dried at 100° C. for 7 h in air atmosphere, calcined at 250° C. for 4 h in air atmosphere, and finally reduced in hydrogen atmosphere at 250° C. for 2 h to obtain a Cu3.5 wt %-CeO₂10 wt %/γ-Al₂O₃@NP catalyst.

The catalysts prepared by the above-mentioned comparative examples 1-5 were respectively used in the following reactions:

2 g of o-nitroaniline, 8 ml of ethanediol, 0.8 g of potassium hydroxide and a catalyst were put into a three-necked flask reactor. The mixture was heated to 80° C. and started to stir (1000 r/min), after stirred at the constant temperature for 6 h, the reaction was stopped, and the reaction solution was cooled to room temperature and filtered to separate the catalyst. The filtrate was extracted and analyzed by gas chromatography, and the experimental results are shown in Table 4, wherein the target product is benzopyrazine.

TABLE 4

Experimental results of one-pot reaction with ethanediol and o-nitroaniline under the action of different catalysts

| comparative example | catalyst | conversion rate (%) | selectivity (%) |
|---|---|---|---|
| 1 | 0.2 g Cu3.5 wt %-Pd5 wt %/γ-Al₂O₃ | 100 | 85.4 |
| 2 | 0.2 g Cu3.5 wt %-Pd5 wt %-CeO₂10 wt %/γ-Al₂O₃ | 100 | 91.2 |
| 3 | 0.2 g Cu3.5 wt %-Pd5 wt %/γ-Al₂O₃@NP | 100 | 88.3 |
| 4 | 0.2 g Pd5 wt %-CeO₂10 wt %/γ-Al₂O₃@NP | 50.1 | 96.8 |
| 5 | 0.2 g Cu3.5 wt %-CeO₂10 wt %/γ-Al₂O₃@NP | 0 | 0 |
| 6 | 0.2 g 5 wt % Pd-CeO₂10 wt %/γ-Al₂O₃@NP + 0.2 g 3.5 wt % Cu-CeO₂10 wt %/γ-Al₂O₃@NP | 59.7 | 92.0 |
| 7 | 0.2 g 3.5 wt % Cu-Pd5 wt %-CeO₂10 wt %/γ-Al₂O₃@NP | 100 | 98.3 |

We claim:

1. A preparation method of a Cu—Pd—CeO₂/γ-Al₂O₃@NP catalyst, in the Cu—Pd—CeO₂/γ-Al₂O₃@NP catalyst, a total loading amounts of N and P is 1.2%~4.8%, a loading amount of Cu is 0.5%~5 wt %, a loading amount of Pd is 0.5%~5 wt %, and a loading amount of Ce is 5%~15 wt %; the preparation method comprises the following steps:
   (1) mixing γ-Al₂O₃ with deionized water, stirring the mixture to obtain a slurry, heating the slurry to 70-90° C., then adding a solution of cerium-containing compound, subjecting the mixture to stirring and impregnation at a constant temperature of 70-90° C. for 2~6 h, adding ammonia water dropwise to adjust the pH value of the solution to 9~10, continuing to stir the resulting solution at the constant temperature for 2-6 h, cooling it to room temperature and filtering it, washing the filter cake with deionized water until the filtrate becomes neutral, drying it at 80~120° C. for 5~9 h in the air, and then calcining it at 600~800° C. for 2~4 h in the air to obtain a CeO₂/γ-Al₂O₃ carrier;
   (2) mixing the CeO₂/γ-Al₂O₃ carrier with an aqueous solution of ammonium phosphate, subjecting the mixture to stirring and impregnation at 30~50° C. for 1~3 hpurs, then drying it at 80-120° C. for 5~9 h in the air, and then calcining the dried product at 400-600° C. for 1-3 hours in the air to obtain a CeO₂/γ-Al₂O₃@NP carrier;
   (3) mixing the CeO₂/γ-Al₂O₃@NP carrier with deionized water, stirring the mixture to obtain a slurry, heated it to 60~100° C., then adding certain amounts of a palladium-containing compound solution and a copper-containing compound solution, subjecting the mixture to stirring and impregnation at the constant temperature for 3~7 h; cooling it to room temperature, adding an alkaline solution dropwise to adjust the pH value to 8~10, stirring the resulting solution at the constant temperature for 0.5~1.5 h, filtering it, washing the filter cake with deionized water until the filtrate becomes neutral; dry it at 80-120° C. in the air for 5-9 h; then calcining the dried product at 200-300° C. for 2-6 h in the air, and finally reducing the calcined product with hydrogen at 200-300° C. for 1~3 h, thereby obtaining the Cu—Pd—CeO₂/γ-Al₂O₃@NP catalyst.

2. The preparation method of claim 1, wherein: in the Cu—Pd—CeO2/γ-Al2O3@NP catalyst, the loading amount of Pd is 1-5 wt %; the loading amount of Cu is 1-5 wt %; and the loading amount of Ce is 10%.

3. The preparation method of claim 2, wherein: in the Cu—Pd—CeO2/γ-Al2O3@NP catalyst, the loading amount of Pd is 5 wt %.

4. The preparation method of claim 2, wherein: in the Cu—Pd—CeO2/γ-Al2O3@NP catalyst, the loading amount of Cu is 3.5%.

5. The preparation method of claim 1, wherein: the palladium-containing compound is H₂PdCl₄, Pd(CH₃COO)₂ or Pd(NO₃)₂; the copper-containing compound is Cu(NO₃)₂ or CuCl₂; and the cerium-containing compound is CeCl₃ or Ce(OH)₃.

6. The preparation method according to claim 1, wherein: in step (1), the feeding ratio of γ-Al₂O₃ to deionized water is 5 g: 35-45 mL, and the concentration of the cerium-containing compound solution calculated as the concentration of Ce is 0.04-0.06 g/mL.

7. The preparation method of claim 1, wherein in step (2), the concentration of the aqueous solution of ammonium phosphate is 0.002-0.0025 g/mL.

8. The preparation method of claim 1, wherein: in step (3), the feeding ratio of the CeO₂/γ-Al₂O₃@NP carrier to deionized water calculated as the feeding ratio of γ-Al₂O₃ to deionized water is 5 g:35-45 mL, the concentration of the palladium-containing compound solution is 0.04-0.05 g/mL in terms of the concentration of Pd, and the concentration of the copper-containing compound solution is 0.04-0.05 g/mL in terms of the concentration of Cu.

9. The preparation method according to claim 1, wherein: in step (3), the alkaline solution is 0.05-0.15 g/ml NaOH aqueous solution, 0.05-0.15 g/ml $NaHCO_3$ aqueous solution or 0.05-0.15 g/ml $Na_2CO_3$ aqueous solution.

10. A one-pot method for synthesizing benzopyrazine compounds of formula (III), which comprises: using an o-nitroaniline compound of formula (I) and an aliphatic diol compound of formula (II) as raw materials, carrying out the one-pot synthesis of the benzopyrazine compound of formula (III) under solvent-free condition and under the combined action of the Cu—Pd—$CeO_2$/γ-$Al_2O_3$@NP catalyst prepared by the method of claim 1 and an alkali;

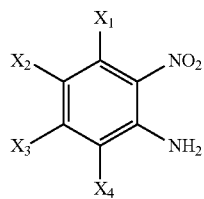

(I)

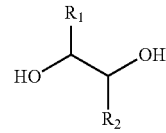

(II)

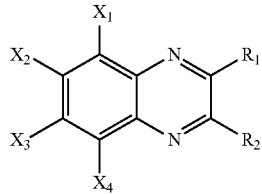

(III)

wherein, $X_1$, $X_2$, $X_3$, $X_4$ are each independently hydrogen, methyl, ethyl or methoxy; $R_1$, $R_2$ are each independently hydrogen, methyl or ethyl.

11. The method of claim 10, wherein: the mass ratio of the Cu—Pd—$CeO_2$/γ-$Al_2O_3$@NP catalyst to the o-nitroaniline compound is 1:5~20; and the molar ratio of the o-nitroaniline compound: the aliphatic diol compound:the alkali is 1:5~15:0.5~2.

12. The method of claim 10, wherein the reaction temperature is 70-90° C.; and the reaction time is 6-12 hours.

13. The method of claim 12, wherein the reaction temperature is 75-85° C.

* * * * *